United States Patent [19]

Nicola et al.

[11] Patent Number: 4,973,592
[45] Date of Patent: Nov. 27, 1990

[54] 1,3-DIAZOCYCLOALKENES AS MUSCARINIC RECEPTOR BLOCKING AGENTS

[75] Inventors: Massimo Nicola, Pavia; Arturo Donetti, Milan; Enzo Cereda, Tortona; Marco Turconi, Voghere; Giovanni B. Schiavi, Asola; Rosamaria Micheletti, Milan, all of Italy

[73] Assignee: Istituto de Angeli, Milan, Italy

[21] Appl. No.: 243,942

[22] Filed: Sep. 13, 1988

[30] Foreign Application Priority Data

Sep. 21, 1987 [IT] Italy .................. 21976 A/87

[51] Int. Cl.$^5$ .................. A61K 31/505; C07D 239/06; C07D 239/12; C07D 239/18
[52] U.S. Cl. .................. 514/269; 514/218; 514/256; 514/272; 514/275; 514/401; 544/242; 544/298; 544/319; 544/320; 544/321; 544/330; 544/332; 544/335; 540/553; 548/347; 548/351; 548/352; 548/353
[58] Field of Search .............. 544/242, 319, 330, 335, 544/298, 320, 321, 332; 514/269, 272, 275, 256

[56] References Cited

U.S. PATENT DOCUMENTS

| | | | |
|---|---|---|---|
| 3,126,381 | 3/1964 | Langis et al. | 544/242 |
| 3,205,232 | 9/1965 | Andress, Jr. et al. | 544/242 |
| 3,483,203 | 12/1969 | Werner | 544/242 |
| 3,502,578 | 3/1970 | Raifsnider | 544/242 |

*Primary Examiner*—Cecilia Shen
*Attorney, Agent, or Firm*—D. E. Frankhouser; M. M. Timbers; A. R. Stempel

[57] ABSTRACT

New pharmacologically active heterocyclic derivatives as muscarinic receptor blocking agents, useful for the treatment of gastrointestinal disorders, of the following formula

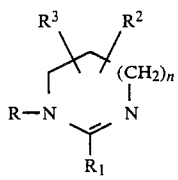

(1)

wherein the substituents are defined hereinbelow.

12 Claims, No Drawings

1,3-DIAZOCYCLOALKENES AS MUSCARINIC RECEPTOR BLOCKING AGENTS

The present invention relates to novel pharmacologically active heterocyclic derivatives, to the process for their preparation and to the pharmaceutical compositions containing them. The new compounds are muscarinic receptor blocking agents useful for the treatment of gastrointestinal disorders.

It is known that the administration of muscarinic receptor blocking agents gives rise to a number of pharmacological effects like decreased gastrointestinal motility, inhibition of acid secretion, dry mouth, mydriasis, urinary incontinence, decreased sweating, tachycardia. Furthermore, antimuscarinic agents with tertiary amine structures may give rise to central effects owing to their penetration into blood-brain barrier. The lack of selectivity among these actions makes it difficult to address therapy in one specific indication and this prompted chemical modification of these agents. One of these modifications consists in quaternization of the tertiary amine function to prevent penetration into the brain. The quaternary drugs lack prominent central actions and additionally show a selective greater effect on the gastro-intestinal tract, while displaying a minor incidence of sideeffects. However their major drawback is the poor and unreliable absorption for oral administration unexploitable for therapeutical purposes. We have now synthetized, and this is the object of the present invention, a new class of heterocyclic derivatives endowed with a strong antimuscarinic activity which showes a further enhanced activity on the gastrointestinal tract associated with a lack of central and peripheral effects such as: mydriasis, tachycardia and dry mouth. Moreover the new heterocyclic derivatives are potentially useful as therapeutically active agents in the management of gastrointestinal motility disorders, such as spastic conditions of the gut, functional diarrhea, constipation, irritable bowel syndrome, cardiospasm, pylorospasm, gastro-oesophageal reflux, peptic ulcer disease, spasm of the urinary and biliary tracts and urinary incontinence. The compounds object of the present invention have the general formula (I)

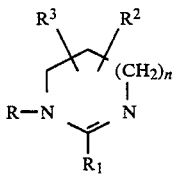
(I)

wherein
R is hydrogen atom or $C_{1-9}$ alkyl optionally substituted by 2 or 3 radicals, which may be identical or different from each other, selected from aryl, cycloalkyl, hydroxy and carboxamide;
$R_1$ may be any group indicated for R, or $NHR_4$, in which $R_4$ is hydrogen atom, $C_{1-4}$ alkyl substituted by $-OOCR_5$, in which $R_5$ is methyl substituted by 2 or 3 radicals, which may be identical or different from each other, selected from aryl, cycloalkyl and hydroxy, or a cycloalkyl substituted by another cycloalkyl;
$R_2$ is hydrogen atom, $C_{1-4}$ alkyl, a radical $-OOCR_5$, in which $R_5$ is as hereinbefore defined;
$R_3$ is hydrogen atom or $C_{1-4}$ alkyl;
n is 0, 1 or 2
provided that at least one among R, $R_1$, $R_2$ and $R_3$ is different from hydrogen atom.

For the pharmaceutical use the compounds (I) are used as such or under the form of tautomers or of physiologically compatible acid addition salts.

The term "acid addition salts" includes salts with inorganic or organic acids. The physiologically compatible acid used for the salification include, for example, maleic, citric, hydrochloric, tartaric, hydrobromic, fumaric, nitric, acetic, sulphuric, methanesulphonic, hydroiodic or formic acid. Although the double bond of the amidine groupments is indicated in the general formula (I) as present in a particular position, other tautomeric forms are also possible. The present invention includes therefore such tautomeric forms as regards both the compounds and the manufacturing process Some compounds of formula (I), according to the present invention, contain one or two asymmetric carbon atoms. The compounds may therefore occur as enantiomers of (+) and (−) type, as diastereoisomers or mixture of them. The present invention includes therefore both the individual isomers and the mixture thereof. It has to be understood that, when mixtures of optical isomers are present, they may be separated according to the classic resolution methods based on their different physico-chemical properties, e.g. by fractional crystallization of their acid addition salts with a suitable optically active acid or by cromatographic separation with a suitable mixture of solvents. In the present invention the term "alkyl" means that it is a straight or branched alkyl group and has 1 to 9 carbon atoms. The term "lower alkyl" means that it is a straight or branched alkyl group and has preferably 1 to 4 carbon atoms. The term "aryl" preferably means phenyl or 4-thiomethylphenyl. The term "cycloalkyl" preferably means that the ring has 3 to 7 carbon atoms. The term "halogen" means fluorine, chlorine, bromine, iodine. The compounds of general formula (I) of the present invention may, for example, be prepared by the following processes, well known in their general lines to the technicians of the branch.

(a) Compounds of general formula (I) wherein R is not a hydrogen atom, $R_1$ is a hydrogen atom or $C_{1-4}$ alkyl, $R_2$ and $R_3$ are hydrogen atoms and n is as hereinbefore defined, may be obtained by reacting a compound of formula (II)

$$R-X \qquad (II)$$

wherein R is as above defined and X represents a leaving group such as halogen, mesyloxy or tosyloxy group, with a compound of general formula (III)

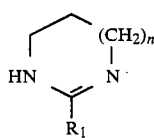
(III)

in which $R_1$ and n are as above defined, in the presence of an inert organic solvent such as lower alcohols, dioxane, dimethylformamide or acetonitrile. The reaction is generally carried out at a temperature from 40° C. to 135° C., preferably 40° C. to 100° C.

The compounds of general formula (II), used as starting materials in the above process, may be obtained by methods that are known per se in the literature, for example by reacting a compound of general formula (IV)

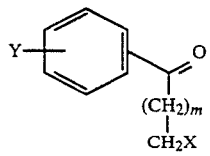

(IV)

wherein Y represents a hydrogen atom, a lower alkoxy, a lower thioalkyl, halogen or cyano, m may be 0–2 and X is as hereinbefore defined, with a Grignard derivative of formula (V)

R₇MgHal    (V)

wherein R₇ represents $C_{1-4}$ alkyl optionally substituted by cycloalkyl group, or cycloalkyl group, and Hal represents chlorine bromine or iodine, in the presence of ether or tetrahydrofurane at a temperature from −70° C. to 40° C.

Optionally the same compounds may be obtained by reacting a compound of formula (II) with a protected alkylenediamine of formula (VI)

$H_2N-CH_2-(CH_2)_n-CH_2-NHP$    (VI)

wherein n is as above defined and P represents a suitable amino-protecting group such as benzyl, benzhydryl, trityl, carbobenzyloxy, p-nitrocarbobenzyloxy in the presence of high-boiling solvents, such as butanol, dimethylformamide or dimethylsulphoxide at a temperature from 50° C., to 180° C., preferably 90° C. to 120° C. The protective group may be removed by using conventional methods, for example by catalytic or transfer hydrogenation, and the intermediate compound so obtained is reacted with formamidine or acetamidine salts. The reaction is conveniently performed in lower alcohols at a temperature between 20° C. and 40° C.

(b) Compounds of general formula (I) wherein $R_1$ is $C_{1-9}$ alkyl optionally substituted by 2 or 3 radicals, which may be identical or different from each other, selected from aryl, cycloalkyl, hydroxy and carboxamide, R is a hydrogen atom or $C_{1-9}$ alkyl, $R_2$ is a hydrogen atom, $R_3$ and n are as hereinbefore defined, may be obtained by reacting a diamine of formula (VII)

$H_2N-CH_2-(CH_2)_n-\underset{R_3}{CH}-NH_2$    (VII)

in which $R_3$ and n are as above defined, with a compound of general formula (VIII)

$\underset{OAlk}{\overset{R_1}{\underset{|}{C}}=NH.HCl}$    (VIII)

wherein $R_1$ is as above defined. The reaction is carried out in an inert solvent such as methylene chloride, ether, chloroform or tetrahydrofuran at a temperature between −5° C. and 30° C. The compound of general formula (VIII), used as starting material in the above process, may be obtained from a nitrile of formula (IX)

$R_1-CN$    (IX)

in which $R_1$ is as above defined, for intramolecular cyclization in the presence of anhydrous hydrochloric acid in an inert solvent such as tetrahydrofuran or ether at a temperature between −20° C. and 30° C.

(c) Compounds of general formula (I) wherein R is a hydrogen atom or $C_{1-9}$ alkyl, $R_1$ is a hydrogen atom or $NH_2$, $R_2$ is $-OOCR_5$ in which $R_5$ is as hereinbefore defined, $R_3$ is a hydrogen atom and n is as hereinbefore defined, may be obtained by reacting a carboxylic acid of formula (X)

$R_5-COOH$    (X)

in which $R_5$ is as above defined, or its reactive derivative such as chloride, with a compound of general formula (XI)

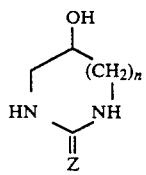

(XI)

wherein Z represents S or $N-NO_2$ and n is as above defined. The reaction is conveniently performed in an inert solvent such as methylene chloride, dimethylformamide or acetonitrile, at a temperature between 20° C. and 60° C., preferably at room temperature and in the presence of a condensing agent such as N,N-carbonyl diimidazole and a strong base such as 1,8-diazabicyclo[5,4,0] undecene or in the presence of a chloride scavenger such as triethylamine or pyridine when the compound of formula (X) is used in the form of acid or its chloride respectively. The intermediate compound so obtained of formula (XII)

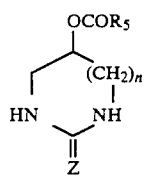

(XII)

when Z is S, is treated with Raney nickel in an inert solvent, for example methylene chloride, at a temperature from 0° C. to 40° C., or, when Z is $N-NO_2$, is reduced by conventional methods such as transfer hydrogenation using formic acid, hydrazine or cyclohexene as hydrogen donors, and palladium as catalyst. Subsequently they may be monoalkylated by alkyl iodide or dialkyl sulphate. A labile group on the acidic moiety may be protected and deprotected during the reaction, for example a hydroxyl group may be converted into a tetrahydropyranyl derivative according to conventional methods and then it may be cleaved by acid hydrolysis (d) Compounds of general formula (I) wherein R and $R_3$ are hydrogen atoms, n is 1, $R_1$ is a hydrogen atom, $C_{1-9}$ alkyl or $NHR_4$, in which $R_4$ is not a hydrogen atom, $R_2$ is a hydrogen atom or $-OOCR_5$ in which $R_5$ is as above defined, may be obtained by reacting a compound of formula (X) or its reactive derivatives such as chloride, with pyrimidinic derivatives of general formula (XIII)

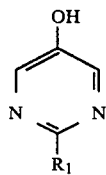
(XIII)

when $R_1$ is a hydrogen atom or $C_{1-9}$ alkyl and $R_2$ is $-OOCR_5$ in which $R_5$ is as above defined, or with a different pyrimidinic derivatives of general formula (XIV)

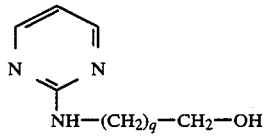
(XIV)

in which q is 1 or 2, when $R_2$ is a hydrogen atom and $R_1$ is $NHR_4$, where $R_4$ is as above defined.

The reaction is conveniently carried out in an inert solvent such as dimethylsulphoxide or dimethylacetamide at a temperature between 20° C. and 60° C., preferably at room temperature and in the presence of a condensing agent such as N,N-carbonyldiimidazole, dicyclohexylcarbodiimide or of a strong base such as sodium hydride when the compound of formula (X) is used in the form of acid or its chloride respectively. The intermediate compound thus obtained is partially reduced by hydrogenation over palladium catalyst. The reaction is carried out at a temperature ranging from 20° C. to 80° C. at a pressure from 1 to 4 atmospheres.

(e) Compounds of general formula (I) wherein R, $R_2$ and $R_3$ are hydrogen atoms, $R_1$ is $NHR_4$ where $R_4$ is not a hydrogen atom and n is as hereinbefore defined, may be obtained by reacting a compound of general formula (XV)

$$R_5COOCH_2-(CH_2)_r-NH_2 \quad (XV)$$

wherein $R_5$ is as hereinbefore defined and r is 1 or 2, with a compound of general formula (XVI)

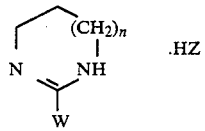
(XVI)

wherein W is a leaving group, such as halogen, mercapto, thiomethyl, thiomethoxy or methylsulphonyl, and Z is halogen or $HSO_4$. The reaction is carried out in water or in polar organic solvent such as methanol, ethanol or dimethylformamide at a temperature ranging from 20° C. to 120° C.

The compounds of general formula (I) prepared according to the processes as above described may optionally be converted with inorganic or organic acids into the corresponding physiologically compatible acid addition salts, for example, by conventional methods such as by reacting the compounds as bases with a solution of the corresponding acid in a suitable solvent. Particularly preferred acids include for example hydrochloric, formic, hydroiodic or acetic acids.

Preferred groups of the compounds, according to the present invention, for their better activity as muscarinic receptor blocking agents are the ones formed by the compounds of general formula (I) wherein:

(a) R represents $C_{1-9}$ alkyl substituted by 3 radicals selected from aryl, cycloalkyl and hydroxy group, $R_1$ represents a hydrogen atom or $C_{1-9}$ alkyl, $R_2$ and $R_3$ are hydrogen atoms and n is 0, 1 or 2;

(b) R represents a hydrogen atom or $C_{1-9}$ alkyl, $R_1$ represents a hydrogen atom or $NH_2$, n is 1, $R_2$ is $-OOCR_5$ where $R_5$ is a methyl group substituted by 3 radicals selected from aryl, cycloalkyl and hydroxy group, and $R_3$ is a hydrogen atom.

As already mentioned hereinbefore the new compounds of formula (I), according to the present invention, have interesting pharmacological properties owing to their ability to antagonize the physiological muscarinic effects in warm blooded animals. Therefore the new compounds are commercially viable in the prevention and in the treatment of motility disorders wherein muscarinic receptors are involved, particularly for spastic conditions of the gastrointestinal tract and irritable bowel syndrome.

The following tests show that the compounds according to the invention have favourable characteristics in this respect.

PHARMACOLOGY

ANTIMUSCARINIC ACTIVITY (in vitro binding studies)

Antimuscarinic activity was examined by studying the displacement of $^3H$-pirenzepine from cerebral cortex homogenate according to the procedure reported below:

The cerebral cortex donors were male CD-COOBBS rats, 220–250 g body weight. The homogenization process was carried out in a Potter-Evelhjem apparatus in the presence of $Na^+/Mg^{++}$HEPES buffer; pH 7.4 (100 mM NaCl, 10 mM $MgCl_2$, 20 mM HEPES), by filtering the suspension through two layers of cheescloth.

Binding curves for the under study compounds were derived indirectly from competition experiments against 0.5 nM $^3H$-pirenzepine labelling the muscarinic receptors of the cerebral cortex. 1 ml of the homogenate was incubated for 45 min at 30° C. in the presence of a marker ligand and different concentrations of the cold ligand, conditions under which equilibrium was reached as determined by appropriate association experiments. The incubation was terminated by centrifugation (12,000 rpm for 3 min) at room temperature using an Eppendorf microcentrifuge. The resultant pellet was washed twice with 1.5 ml saline to remove the free radioactivity and it was allowed to drain for some hours.

The tips of the tubes containing the pellet were cut off and 200 μl of tissue solubilizer (Lumasolve, Lumac) were added and left to stand overnight. Radioactivity was then counted after addition of 4 ml of liquid scintillation mixture (Dimilume/Toluene 1:10 v:v, Packard)

Assays were carried out in triplicate or quadruplicate and the non-specific binding was defined as the radioactivity bound or entrapped in the pellet when the incubation medium contained 1 μM atropine sulphate. Non-specific binding avarage less than 30%. $K_D$ values (dissociation constants) were obtained by non-linear regression analysis on the basis of a one binding site model with TOPFIT-pharmacokinetic programme package (G. HEINZEL, "Pharmacokinetics during drug development: data analysis and evaluation techniques" Eds. G. BOLZER and J. M. VAN ROSSUM; p. 207, G. Fisher, New York, 1982) after correction for the radioligand occupancy shift according to the equation: $K_D = IC_{50}/1 + {}^*C/{}^*K_D$, where ${}^*C$ and ${}^*K_D$ represent the concentration and the dissociation constant of the radioligand used, respectively.

The following table 1 shows the obtained results:

TABLE 1

Antimuscarinic effect. Dissociation constants ($K_D$) for ³H-pirenzepine binding

| Compound | $K_D$ (nM) |
|---|---|
| 1 | 4.2 |
| 2 | 3 |
| 10 | 4.5 |
| 11 | 9 |
| 14 | 3.2 |
| 15 | 2.7 |
| 21 | 7.4 |
| 22 | 5 |
| 23 | 14 |

ANTISPASMODIC ACTIVITY

Antispasmodic activity of the compounds was tested on isolated guinea pig ileum with bethanechol as a spasmogen according to the method as described in Edinburgh Staff ("Pharmacological Experiments on Isolated Preparations" Second edition, Churchill Livingstone, Edimburgh, 1974).

Guinea pigs (450-55 g, Dunkin Hartley) were sacrified by cervical dislocation, and a 2 cm piece of terminal ileum was rapidly excised. The tissue was mounted in a 10 ml organ bath containing Tyrode solution of the following composition (mM) NaCl 137; KCl 2.68; $CaCl_2$ 1.82; $NaHCO_3$ 5.9; $MgCl_2$ 1; $NaH_2PO_4$ 0.42; glucose 5.6. Temperature was 37° C., resting tension 800 mg. Contractions were induced by cumulative addition of bethanechol (0.3-30 μM), each concentration being left in contact until maximal response was observed. Antagonists were added to the bath 60 min before repeating agonist stimulation.

The shift of bethanechol concentration-response curve induced by antagonists, dose-ratio (DR), was calculated by a computer programme (Tallarida, R. S., and Murray, R. B. "Manual of Pharmacologic Calculations with Computer Programs" Springer Verlag, New York, 1981) after verifying parallelism. $K_B$ (dissociation constant) was estimated by linear regression analysis as:

$$K_B = \frac{[B]}{DR - 1}$$

where [B] represents the concentration of the antagonist under study.

The results are reported in the following table II:

TABLE 11

Antispasmodic activity. Dissociation constants ($K_B$) for bethanechol induced contractions in the guinea pig ileum

| Compound | $K_B$ (nM) |
|---|---|
| 1 | 1 |
| 2 | 1.7 |

TABLE 11-continued

Antispasmodic activity. Dissociation constants ($K_B$) for bethanechol induced contractions in the guinea pig ileum

| Compound | $K_B$ (nM) |
|---|---|
| 10 | 1.4 |
| 11 | 2 |
| 14 | 0.32 |
| 15 | 0.46 |
| 21 | 3.4 |
| 22 | 1.5 |
| 23 | 6.2 |

According to a further feature of the present invention there are provided pharmaceutical compositions comprising as active ingredient at least one compound of formula (I), as hereinbefore defined, or a physiologically compatible acid addition salt thereof in association with a pharmaceutical carrier or excipient. For pharmaceutical administration the compounds of general formula (I) and their physiologically compatible acid addition salts may be incorporated into the conventional pharmaceutical preparations in either solid or liquid form. The compositions may, for example, be presented in a form suitable for oral, rectal or parenteral administration. Preferred forms include, for example, capsules, tablets, coated tablets, freeze-dried vials, suppositories and oral drops.

The active ingredient may be incorporated in excipients or carrier conventionally used in pharmaceutical compositions such as, for example, talc, gum arabic, lactose, gelatine, magnesium stearate, corn starch, aqueous or non-aqueous vehicles, polyvinylpirrolidone, mannitol, semisynthetic glicerides of fatty acids, sorbitol, propylene glycol, citric acid, sodium citrate. The compositions are advantageously formulated at dosage units, each dosage unit being adapted to supply a single dose of the active ingredient. Each dosage unit may conveniently contain from 5 mg to 500 mg and preferably from 10 mg to 100 mg.

The following examples illustrate some of the new compounds according to the present invention; these examples are not to be considered in any way limitative of the scope of the invention itself:

EXAMPLE 1

1-(3-Phenyl-3-cyclohexyl-3-hydroxy)propyl-1,4,5,6-tetrahydropyrimidine hydrochloride (Compound 1)

A mixture of 1-phenyl-1-cyclohexyl-3-chloro-1-propanol (1.26 g) and 3,4,5,6-tetrahydropyrimidine (0.42 g) in 15 ml of anhydrous dimethylformamide (DMF) was heated at 75°-80° C. for 30 hours. The solvent was evaporated in vacuum and the residue was purified by column chromatography (eluent methanol, acetic acid, aqueous ammonia 100:2:3). The collected fractions were evaporated, the residue taken up with methylene chloride and washed by water. Evaporation of the solvent afforded the desired compound as the free base, which was treated with ethanolic HCl to obtain 0.5 g of 1-(3-phenyl-3-cyclohexyl-3-hydroxy)propyl-1,4,5,6-tetrahydropyrimidine hydrochloride. M.p. 203°-205° C. M S (C.I.): 301 m/e [M+H]+

| Analysis | | | | |
|---|---|---|---|---|
| $C_{19}H_{28}N_2O \cdot HCl$ | Found % | C 67.51 | H 8.62 | N 8.38 |
| | Calc. % | C 67.74 | H 8.68 | N 8.32 |

According to the procedure above described the following compound was also prepared:

1-(3-Phenyl-3-cyclohexyl-3-hydroxy)propyl-2-methyl-2-imidazoline hydrochloride (Compound 2)

M.p. 231°–233° C.
M S (C.I.): 301 m/e [M+H]+:

| Analysis | Found % | C 67.59 | H 8.70 | N 8.36 |
|---|---|---|---|---|
| $C_{19}H_{28}N_2O\cdot HCl$ | Calc. % | C 67.74 | H 8.68 | N 8.32 |

EXAMPLE 2

2-(3-Phenyl-3-cyclohexyl-3-hydroxy)propyl-1,4,5,6-tetrahydropyrimidine hydrochloride (Compound 3)

(a) A mixture of 1-phenyl-1-cyclohexyl-3-chloro-1-propanol (3.8 g) and sodium cyanide (0.69 g) in 11 ml of dimethyl sulphoxide (DMSO) was heated at 140° C. for 3 hours. The mixture was poured into ice, then the water was extracted with ether. The solvent was removed and the residue triturated with diisopropylic ether to afford 2.7 g of 1-phenyl-1-cyclohexyl-3-cyano-1-propanol. M.p. 97°–101° C.

(b) To an ice-cooled solution of 1-phenyl-1-cyclohexyl-3-cyano-1-propanol (1.4 g) in anhydrous tetrahydrofuran (THF), a solution of HCl 10% w/v in ether (2.5 ml) was added dropwise. The mixture was stirred and cooled for 48 hours. The solvent was removed and the residue triturated with diethyl ether/THF to afford 0.8 g of 2-imino-5-phenyl-5-cyclohexyltetrahydrofuran hydrochloride. M.p. 100°–102° C.

(c) A solution of 2-imino-5-phenyl-5 cyclohexyltetrahydrofuran hydrochloride (0.31 g) and 1,3-diaminopropane (0.09 ml) in chloroform (10 ml) was stirred at room temperature overnight. The solid was filtered and crystallized from isopropanol to afford 0.22 g of 2-(3-phenyl-3-cyclohexyl-3-hydroxy)propyl-1,4,5,6-tetrahydropyrimidine hydrochloride. M.p. 251°–252° C.
M S (C.I.): 301 m/e M+H+.

| Analysis | Found % | C 67.70 | H 8.74 | N 8.32 |
|---|---|---|---|---|
| $C_{19}H_{28}N_2O\cdot HCl$ | Calc. % | C 67.74 | H 8.68 | N 8.32 |

According to the procedure above described the following compounds were also prepared:

2-(3-Phenyl-3-cyclohexyl-3-hydroxy)propyl-2-imidazoline hydrocloride (Compound 4)

M.p. 197°–198° C.
M S (C.I.): 287 m/e [M+H]+

| Analysis | Found % | C 66.88 | H 8.46 | N 8.73 |
|---|---|---|---|---|
| $C_{18}H_{26}N_2O\cdot HCl$ | Calc. % | C 66.96 | H 8.43 | N 8.68 |

1-Methyl-2-(3-phenyl-3-cyclohexyl-3-hydroxy)propyl-1,4,5,6-tetrahydropyrimidine hydrochloride (Compound 5)

M.p. 168°–170° C.
M S (C.I.): 315 m/e [M+H]+.

| Analysis | Found % | C 68.51 | H 8.89 | N 8.01 |
|---|---|---|---|---|
| $C_{20}H_{30}N_2O\cdot HCl$ | Calc. % | C 68.45 | H 8.90 | N 7.98 |

2-(3-Phenyl-3-cyclohexyl-3-hydroxy)propyl-4(5)-methyl-2-imidazoline hydrochloride (Compound 6)

M.p. 93°–96° C. (dec.).
M S (C.I.): 301 m/e [M+H]+.

| Analysis | Found % | C 67.80 | H 8.69 | N 8.30 |
|---|---|---|---|---|
| $C_{19}H_{28}N_2O\cdot HCl$ | Calc. % | C 67.74 | H 8.68 | N 8.32 |

2-(3-Phenyl-3-cyclohexyl-3-hydroxy)propyl-1H-4,5,6,7-tetrahydrodiazepine hydrochloride (Compound 7)

M.p. 202°–204° C.

EXAMPLE 3

1,4,5,6-Tetrahydropyrimidin-5-yl mandelate hydrochloride (Compound 8)

(a) To a solution of α-(tetrahydropyran-2-yloxy)-phenylacetic acid (2.74 g) and N,N-carbonyldiimidazole (1.88 g) in DMF (8.5 ml), 5-hydroxy-1H-hexahydropyrimidine-2-thione (1.54 g) and 1,8-diazabicyclo [5.4.0] undec-7-ene (DBU) (1.77 g) were added. The mixture was stirred at room temperature overnight, then poured into water. The aqueous phase was extracted with ethyl acetate. Evaporation of the solvent and trituration of the residue with di-isopropyl ether afforded 2 g of the desired 1H-hexahydropyrimidin-5-yl-2-thione α-(tetrahydropyran-2-yl) phenylacetate. M.p. 52°–60° C.

(b) A solution of 1H-hexahydropyrimidin-5-yl-2-thione α-(tetrahydropran-2-yl)phenyl acetate (2 g) in 10% aqueous HCl (5 ml) and ethanol (3 ml) was stirred at room temperature for 2 hours. The ethanol was evaporated and the water solution was extracted with methylene chloride. The organic solvent was evaporated and the residue purified by column chromatography (eluent methylene chloride/methanol 95:5). Evaporation of the solvent afforded 1H-hexahydropyrimidin-5-yl-2-thione mandelate. M.p. 178° C.

According to the procedure above described the following intermediates were also obtained:
1H-Hexahydropyrimidin-5-yl-2-thione diphenylacetate. M.p. 152° C.
1H-Hexahydropyrimidin-5-yl-2-thione α-cyclohexylphenylglycolate. M.p. 157°–158° C.
1H-Hexahydropyrimidin-5-yl-2-thione α-cyclopentylphenylglycolate. M.p. 75°–85° C.

(c) A mixture of 1H-hexahydropyrimidin-5-yl-2-thionemandelate (0.15 g) and Raney-nickel (1 g) in methylene chloride (10 ml) was stirred at room temperature for 90 minutes. The catalyst was filtered off, ethanolic HCl was added and the solvent was removed affording 0.1 g of 1,4,5,6-tetrahydropyrimidin-5-yl mandelate hydrochloride. M.p. 85°–90° C. (dec.).
M S (C.I.): 235 m/e [M+H]+.

| Analysis | Found % | C 53.19 | H 5.60 | N 10.38 |
|---|---|---|---|---|

-continued

| | | C | H | N |
|---|---|---|---|---|
| $C_{12}H_{14}N_2O_3 \cdot HCl$ | Calc. % | C 53.24 | H 5.59 | N 10.35 |

According to the procedure above described the following compounds were also obtained:

1,4,5,6-Tetrahydropyrimidin-5-yl diphenylacetate hydrochloride (Compound 9)

M.p. 105°–110° C.
M S (C.l.): 295 m/e [M+H]+.

| Analysis | Found % | C 65.42 | H 5.80 | N 8.42 |
|---|---|---|---|---|
| $C_{18}H_{18}N_2O_2 \cdot HCl$ | Calc. % | C 65.35 | H 5.79 | N 8.47 |

1,4,5,6-Tetrahydropyrimidin-5-yl α-cyclohexylphenylglycolate hydrochloride (Compound 10)

M.p. 162°–164° C.
M S (C.l.): 317 m/e [M+H]+.

| Analysis | Found % | C 61.30 | H 7.14 | N 7.99 |
|---|---|---|---|---|
| $C_{18}H_{24}N_2O_3 \cdot HCl$ | Calc. % | C 61.26 | H 7.14 | N 7.94 |

1,4,5,6-Tetrahydropyrimidin-5-yl α-cyclopentylglycolate hydrochloride (Compound 11)

M.p. 75°–80° C.
M S (C.l.): 303 m/e [M+H]+.

| Analysis | Found % | C 59.96 | H 6.85 | N 8.03 |
|---|---|---|---|---|
| $C_{17}H_{22}N_2O_3 \cdot HCl$ | Calc. % | C 60.26 | H 6.84 | N 8.26 |

This compound was treated with dimethyl sulphate in ethanol to afford

1-Methyl-1,4,5,6-tetrahydropyrimidin-5-yl α-cyclopentylglycolate hydrochloride (Compound 12)

M.p. 60° C.
M S (C.l.): 317 m/e [M+H]+.

| Analysis | Found % | C 61.13 | H 7.09 | N 8.00 |
|---|---|---|---|---|
| $C_{18}H_{24}N_2O_3 \cdot HCl$ | Calc. % | C 61.26 | H 7.14 | N 7.94 |

EXAMPLE 4

2-Methyl-1,4,5,6-tetrahydropyrimidin-5yl 1-cyclohexylcyclohexane-1-carboxylate hydrochloride (Compound 13)

(a) To an ice-cooled mixture of 2-methyl-5hydroxypyrimidine (0.9 g) and sodium hydride 80% (0.24 g) in dimethylacetamide (15 ml), a solution of 1-cyclohexylcyclohexane-1-carbonyl chloride (1.68 g) in dimethylacetamide (10 ml) was added. The mixture was then stirred at room temperature for 1 hour, then filtered and evaporated in vacuo. The residue was taken up with ethyl acetate, which was washed with water and dried. Evaporation of the solvent and column chromatography (cyclohexane/ethyl acetate 9:1) afforded 1.2 g of 2-methylpyrimidin-5-yl 1-cyclohexylcyclohexane-1-carboxylate. M.p. 52°–55° C. According to the procedure above described the following compound was also prepared, 2-methylpyrimidin-5-yl α-cyclopentylphenyl glicolate hydrochloride. M.p. 132°–138° C.

(b) A mixture of 2-methylpyrimidin-5-yl 1-cyclohexylcyclohexane1-carboxylate hydrochloride and 10% palladium on carbon (0.12 g) in ethanol (10 ml) was hydrogenated at room pressure. After the hydrogen absorption had ceased, the catalyst was filtered off and the solvent was evaporated in vacuo. The residue was purified by column chromatography (methylene chloride/methanol/water 80:20:2) to give 0.43 g of 2-methyl-1,4,5,6-tetrahydropyrimidin 5-yl 1-cyclohexylcyclohexane-1-carboxylate hydrochloride. M.p. 212°–214° C.
M S (C.l.): 307 m/e [M+H]+.

| Analysis | Found % | C 62.89 | H 9.09 | N 8.19 |
|---|---|---|---|---|
| $C_{18}H_{30}N_2O_2 \cdot HCl$ | Calc. % | C 63.04 | H 9.11 | N 8.17 |

According to the procedure above described, the following compound was prepared:

2-Methyl-1H-1,4,5,6-tetrahydropyrimidin-5-yl α-cyclopentylphenylglycolate hydrochloride (Compound 14)

M.p. >200° C.
M S (C.l.): 317 m/e [M+H]+.

| Analysis | Found % | C 60.89 | H 7.13 | N 7.88 |
|---|---|---|---|---|
| $C_{18}H_{24}N_2O_3 \cdot HCl$ | Calc. % | C 61.26 | H 7.14 | N 7.94 |

EXAMPLE 5

2-Amino-1,4,5,6-tetrahydropyrimidin-5-yl 1-cyclohexylcyclohexane-1-carboxylate formate (Compound 15)

(a) To a solution of 1-cyclohexylcyclohexane-1-carbonyl chloride (2.1 g) in acetonitrile (30 ml), 5-hydroxy-2-nitroiminohexahydropirimidine (1.28 g) was added portionwise. The mixture was stirred at room temperature overnight, then DMF (10 ml) was added and the mixture was heated to 50° C. for 24 hours. The reaction was quenched with water. The precipitate was collected, dried and triturated with diethyl ether to afford 0.93 g of 2-nitroiminohexahydropyrimidin-5-yl 1-cyclohexylcyclohexane-1-carboxylate.

M.p. 218°–220° C. According to the procedure above described the following intermediates were obtained:
2-Nitroiminohexahydropyrimidin-5-yl diphenylacetate, M.p. 196°–197° C.
2-Nitroiminohexahydropyrimidin-5-yl α-cyclohexylphenylglicolate, M.p. 205°–207° C.

(b) To a mixture of 2-nitroiminohexahydropyrimidin-5-yl diphenylacetate (0.4 g) and methyl iodide (0.16 g) in DMF (4 ml), 80% sodium hydride (0.06 g) was added. The mixture was then stirred at room temperature overnight. The solvent was removed and the residue taken up with methylene chloride/water. The organic layer was evaporated and the residue was purified by column chromatography (eluent methylene chloride/methanol 98:2) to afford 1-methyl-2-nitroiminohexahydropyrimidin-5-yl diphenylacetate. M.p. 187° C.

(c) A solution of 2-nitroiminohexahydropyrimidin-5-yl 1-cyclohexylcyclohexane-1-carboxylate (0.45 g) in formic acid (20 ml) was quickly dropped into a flask containing 10% palladium on carbon (0.4 g). The reaction mixture was stirred at room temperature overnight. The catalyst was filtered off, the solvent was removed and the residue was triturated with diethyl ether, affording 0.35 g of 2-amino-1,4,5,6-tetrahydropyrimidin-5-yl 1-cyclohexylcyclohexane-1-carboxylate formate. M.p. 160°–165° C. (dec.).

M S (C.I.): 340 m/e [M+H]+.

| Analysis | | | | | | | |
|---|---|---|---|---|---|---|---|
| $C_{17}H_{29}N_3O_2 \cdot HCOOH$ | Found % | C | 58.43 | H | 8.45 | N | 11.40 |
| | Calc. % | C | 58.51 | H | 8.46 | N | 11.37 |

According to the procedure above described the following compounds were obtained:

2-Amino-1,4,5,6-tetrahydropyrimidin-5-yl diphenylacetate hydrochloride (Compound 16)

M.p. 222°–225° C.
M S (C.I.): 310 m/e [M+H]+.

| Analysis | | | | | | | |
|---|---|---|---|---|---|---|---|
| $C_{18}H_{19}N_3O_2 \cdot HCl$ | Found % | C | 62.49 | H | 5.82 | N | 12.12 |
| | Calc. % | C | 62.52 | H | 5.83 | N | 12.15 |

1-Methyl-2-amino-1,4,5,6-tetrahydropyrimidin-5-yl diphenylacetate hydrochloride (Compound 17)

M.p. 240° C.
M S (C.I.): 324 m/e [M+H]+.

| Analysis | | | | | | | |
|---|---|---|---|---|---|---|---|
| $C_{19}H_{21}N_3O_2 \cdot HCl$ | Found % | C | 63.38 | H | 6.17 | N | 11.71 |
| | Calc. % | C | 63.42 | H | 6.16 | N | 11.68 |

2-Amino-1,4,5,6-tetrahydropyrimidin-5-yl α-cyclohexylphenylglicolate formate (Compound 18)

M.p. 88°–90° C.
M S (C.I.): 332 m/e [M+H]+.

| Analysis | | | | | | | |
|---|---|---|---|---|---|---|---|
| $C_{18}H_{25}N_3O_3 \cdot HCOOH$ | Found % | C | 60.37 | H | 7.19 | N | 11.12 |
| | Calc. % | C | 60.45 | H | 7.21 | N | 11.13 |

EXAMPLE 6

2-(1,4,5,6,-Tetrahydropyrimidin-2-yl)aminoethyl α-cyclohexylphenylglycolate hydrochloride (Compound 19)

(a) To a mixture of α-cyclohexylphenylglycolic acid (1 g) and N,N-carbonyldiimidazole (0.69 g) in DMF (10 ml), 2-(2-hydroxyethyl) aminopyrimidine (0.6 g) and DBU (0.65 g) were added. The mixture was treated according to the method described in Example 3a, affording 2-(2-pyrimidyl)aminoethyl α-cyclohexylphenylglycolate, which was heated with ethanolic HCl to afford 1,5 g of the hydrochloride. M.p. 167°–168° C.

(b) A mixture of 2-(2-pyrimidyl)aminoethyl α-cyclohexylphenylglycolate hydrochloride (1.4 g) and 10% palladium on carbon (0.15 g) in H2O (150 ml), was hydrogenated at room pressure. After the absorption had ceased, the catalyst was filtered off, and the solution was evaporated in vacuo. The residue was triturated with ethylacetate, affording 0.85 of 2-(1,4,5,6-tetrahydropyrimidin-2-yl)aminoethyl α-cyclohexylphenylglycolate hydrochloride. M.p. 95° C.

M S (C.I.): 360 m/e [M+H]+.

| Analysis | | | | | | | |
|---|---|---|---|---|---|---|---|
| $C_{20}H_{29}N_3O_3 \cdot HCl$ | Found % | C | 60.73 | H | 7.61 | N | 10.59 |
| | Calc. % | C | 60.67 | H | 7.64 | N | 10.61 |

EXAMPLE 7

2-(2-Imidazolin-2-yl)aminoethyl 1-cyclohexylcyclohexane-1-carboxylate hydroiodide (Compound 20)

A solution of 2-aminoethyl 1-cyclohexylcyclohexane-1-carboxylate (2.5 g) and 2-methylthio-2-imidazoline hydroiodide (2.4 g) in methanol (50 ml) and water (30 ml) was heated at 80° C. for 8 hours. The reaction mixture was evaporated to dryness, and from the residue, after trituration with cyclohexane, 2.3 g of the title compound were obtained. M.p. 134°–136° C.

M S (C.I.): 322 m/e [M+H]+

| Analysis | | | | | | | |
|---|---|---|---|---|---|---|---|
| $C_{18}H_{31}N_3O_2 \cdot HI$ | Found % | C | 48.38 | H | 7.25 | N | 41.97 |
| | Calc. % | C | 48.42 | H | 7.22 | N | 42.03 |

EXAMPLE 8

1-(4-Phenyl-4-cyclohexyl-4-hydroxy)butyl-2-methyl-2-imidazoline hydrochloride (Compound 21)

(a) To a stirred and ice-cooled solution of cyclohexyl magnesium chloride (60 mmol) in dry ether (23.2 ml), 4-chlorobutyrophenone (5.5 g) in ether (17 ml) was added dropwise. The mixture was stirred at 0° C. for 2 hours, then an aqueous solution of sodium chloride was cautiously added. The organic phase was separated and dried. The solvent was removed and the residue was purified by column chromatography (hexane, ether 98:2), affording 5 g of 1-phenyl-1-cyclohexyl-4-chloro-1-butanol as an oil.

M S (C.I.): 267 m/e [M+H]+

According to the procedure above described the following intermediates were obtained:
2-(4-Thiomethyl)phenyl-1-cyclohexyl-4-chloro-2-butanol
1-(4-Thiomethyl)phenyl-1-cyclohexyl-4-chloro-1-butanol
2,2-Diphenyl-4-chlorobutanamide
1-chloro-3-phenyl-3-heptanol.

(b) A mixture of 1-phenyl-cyclohexyl-4-chloro-1-butanol and 2-methyl-2-imidazoline in DMF was treated according to the method described in Example 1, obtaining 1-(4-Phenyl-4-cyclohexyl-4-hydroxy)butyl- 2-methyl-2-imidazoline hydrochloride. M.p. 185°–188° C.

M S (C.I.): 315 m/e [M+H]+.

| Analysis | | | | | | | |
|---|---|---|---|---|---|---|---|
| C20H30N2O.HCl | Found % | C | 68.40 | H | 8.88 | N | 8.01 |
| | Calc. % | C | 68.45 | H | 8.90 | N | 7.98 |

According to the procedure above described, the following compound was obtained:

1-(4-Phenyl-4-cyclohexyl-4-hydroxy)butyl-1,4,5,6-tetrahydropyrimidine hydrochloride (Compound 22)

M.p. 227°–229° C.
M S (C.I.): 315 m/e [M+H]+.

| Analysis | | | | | | | |
|---|---|---|---|---|---|---|---|
| C20H30N2O.HCl | Found % | C | 68.37 | H | 8.87 | N | 8.02 |
| | Calc. % | C | 68.45 | H | 8.90 | N | 7.98 |

EXAMPLE 9

1-(3-phenyl-3-cyclohexyl-3-hydroxy)propyl-2-imidazoline hydrochloride (Compound 23)

(a) To a mixture of N-tritylethylenediamin (3.66 g) and sodium carbonate (9.2 g) in n-butanol (20 ml), a solution of 1-phenyl-1-cyclohexyl-3-chloro-1-propanol (3 g) in butanol (10 ml) was added. The mixture was refluxed overnight, then cooled, diluted with water and extracted with ethyl acetate. The solvent was dried and evaporated. The residue was purified by column chromatography (methylene chloride, methanol, ammonia 99:1:0.1) to afford 3.8 g of 1-phenyl-1-cyclohexyl-3-(2-tritylaminoethyl)amino-1-propanol. M.p. 198° C.

According to the procedure above described, the following intermediates were also obtained:

1-Phenyl-1-cyclohexyl-3-(3-tritylaminopropyl)amino-1-propanol, M.p. 95°–100° C. 1-Phenyl-1-cyclohexyl-3-(4-tritylaminobutyl)amino-1-propanol, M S (C.I.): 559 m/e [M+H]+.

1-Phenyl-1-cyclohexyl-4-(4-tritylaminobutyl)amino-1-butanol.

(b) A solution of 1-phenyl-1-cyclohexyl-3-(2-tritylaminoethyl) amino-1-propanol in methanol/acetic acid 10:1 was hydrogenated over 10% palladium on carbon at room pressure. After the absorption had ceased the catalyst was filtered off, ethanolic HCl was added and the solvent was evaporated. Trituration with ether afforded 1-phenyl-1-cyclohexyl-3-(2-aminoethyl)amino-1-propanol hydrochloride. M.p. 134°–137° C.

According to the procedure above described, the following intermadiates were also obtained:

1-Phenyl-1-cyclohexyl-3-(3-aminopropyl)amino-1-propanol hydrochloride. M S (C.I.): 291 m/e [M+H]+

1-Phenyl-1-cyclohexyl-3-(4-aminobutyl)amino-1-propanol hydrochloride.

1-Phenyl-1-cyclohexyl-4-(4-amonobutyl)amino-1-butanol hydrochloride.

(c) A mixture of 1-phenyl-1-cyclohexyl-3-(2-aminoethyl)-amino-1-propanol, as free base, (0.35 g) and formamidine acetate (0.13 g) in ethanol was stirred at room temperature for 2.5 hours. Treatment with ethanolic HCl, evaporation of the solvent and trituration with ethyl acetate gave 0.2 g of 1-(3-phenyl-3-cyclohexyl-3-hydroxy)propyl-2-imidazoline. M.p. 177°–179° C.

M S (C.I.): 287 m/e [M+H]+

| Analysis | | | | | | | |
|---|---|---|---|---|---|---|---|
| C18H26N2O.HCl | Found % | C | 66.66 | H | 8.40 | N | 8.71 |
| | Calc. % | C | 66.96 | H | 8.43 | N | 8.68 |

According to the procedure above described, the following compound was obtained:

2-Methyl-1-(3-phenyl-3-cyclohexyl-3-hydroxy)propyl-1,4,5,6-tetrahydropyrimidine hydrochloride (Compound 24)

M.p. 203°–205° C.
M S (C.I.): 315 m/e [M+H]+.

| Analysis | | | | | | | |
|---|---|---|---|---|---|---|---|
| C20H30N2O.HCl | Found % | C | 68.38 | H | 8.89 | N | 7.95 |
| | Calc. % | C | 68.45 | H | 8.90 | N | 7.98 |

The following not limitative examples of pharmaceutical compositions according to the invention are reported:

EXAMPLE 10

| active ingredient | 20 mg |
|---|---|
| lactose | 247 mg |
| corn starch | 30 mg |
| magnesium stearate | 3 mg |

Method of preparation: The active ingredient, lactose, and corn starch were mixed and homogeneously moistened with water. After screening of the moist mass and drying in a tray drier, the mixture was again passed through a screen and magnesium stearate was added. Then the mixture was pressed into tablets weighing 300 mg each. Each tablet contains 20 mg of active ingredient.

EXAMPLE 11

| Capsules | |
|---|---|
| active ingredient | 20 mg |
| lactose | 178 mg |
| magnesium stearate | 2 mg |

Method of preparation: the active ingredient was mixed with the auxiliary products, and the mixture was passed through a screen and mixed homogeneously in a suitable device. The resulting mixture was filled into hard gelatine capsules (200 mg per capsule); each capsule contains 20 mg of active ingredient.

EXAMPLE 12

| Freeze-dried vials | |
|---|---|
| active ingredient | 10 mg |
| mannitol | 50 mg |

Method of preparation: the active ingredient and mannitol were dissolved in an appropriate amount of water for injection. The resulting solution was filtered and filled into vials under sterile conditions. The vials were freeze-dried and stopped with a suitable closure.

EXAMPLE 13

| Suppositories | |
|---|---|
| active ingredient | 50 |
| semisynthetic glicerides of fatty acids | 750 mg |

Method of preparation: the semisynthetic gliceride of fatty acids were melted and the active ingredient was added while stirring homogeneously. After cooling at a proper temperature the mass was poured into preformed moulds for suppositories weighing 800 mg each. Each suppository contains 50 mg of active ingredient.

EXAMPLE 14

| Oral drops | |
|---|---|
| active ingredient | 10 mg |
| sorbitol | 350 mg |
| propylene glycol | 200 mg |
| citric acid | 1 mg |
| sodium citrate | 3 mg |
| demineralized water q.s | 1 ml |

Method of preparation: the active ingredient, citric acid and sodium citrate were dissolved in a mixture of a proper amount of water and propylene glycol. Then sorbitol was added and the final solution was filtered. The solution contains 1% of active ingredient and is administered by using a proper dropper.

What is claimed is:

1. A compound of formula (1)

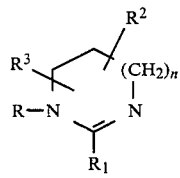

(1)

wherein

R is hydrogen or $C_{1-9}$ alkyl optionally substituted by 2 or 3 radicals, which may be identical or different from each other, selected from phenyl, $C_{3-7}$ cycloalkyl, hydroxy and carboxamide;

$R_1$ may be any group indicated for R, or $NHR_4$, in which $R_4$ is hydrogen, $C_{1-4}$ alkyl substituted by $-OOCR_5$ in which $R_5$ is methyl substituted by 2 or 3 radicals, which may be identical or different from each other, selected from phenyl, $C_{3-7}$ cycloalkyl and hydroxy, or a $C_{3-7}$ cycloalkyl substituted by another $C_{3-7}$ cycloalkyl;

$R_2$ is hydrogen, $C_{1-4}$ alkyl, a radical $-OOCR_5$, in which $R_5$ is as hereinbefore defined;

$R_3$ is hydrogen or $C_{1-4}$ alkyl;

n is 1 provided that at least one among R, $R_1$, $R_2$ and $R_3$ is different from hydrogen, a tautomer thereof and an acid addition salt of the aforesaid compound.

2. The pharmaceutically acceptable acid addition salt of a compound of formula (1) as recited in claim 1.

3. The salt as recited in claim 2 characterized in that the pharmaceutically acceptable acid is hydrochloric, hydroiodic, formic or acetic acid.

4. The compound of formula (1) as recited in claim 1 characterized in that R is $C_{1-9}$ alkyl trisubstituted by phenyl, $C_{3-7}$ cycloalkyl or hydroxy, $R_1$ is hydrogen or $C_{1-9}$ alkyl, $R_2$ and $R_3$ are hydrogen and n is 1, a tautomer thereof and an acid addition salt of the aforesaid compound.

5. The compound of formula (1), according to claim 1 characterized in that R is hydrogen, $R_1$ is hydrogen or $NH_2$, n is 1, $R_2$ is $-OOCR_5$ where $R_5$ is a methyl group trisubstituted by $C_{3-7}$ cycloalkyl or hydroxy and $R_3$ is hydrogen, a tautomer thereof and an acid addition salt thereof.

6. The pharmaceutically acceptable acid addition salt of a compound of formula (1) as recited in claim 4.

7. The salt as recited in claim 6 characterized in that the pharmaceutically acceptable acid is hydrochloric, hydroiodic, formic or acetic acid.

8. The pharmaceutically acceptable acid addition salt of a compound of formula (1) as recited in claim 5.

9. The salt as recited in claim 8 is hydrochloride, hydroiodic, formate or acetate.

10. An antimuscarinic pharmaceutical composition comprising from about 10 to 100 mg of a compound as recited in claim 1 in association with one or more pharmaceutically acceptable carrier or excipients.

11. A method for treating gastrointestinal motility disorders in a warm-blooded animal which comprises administering to said animal a therapeutically effective amount of a compound as recited in claim 1.

12. A method for treating spasm of the biliary tract in a warm-blooded animal which comprises administering to said animal a therapeutically effective amount of a compound as recited in claim 1.

* * * * *